(12) United States Patent
Metzinger et al.

(10) Patent No.: US 8,241,286 B2
(45) Date of Patent: Aug. 14, 2012

(54) METHOD FOR IMPLANTING A HIP FRACTURE NAIL SYSTEM

(75) Inventors: Anthony J. Metzinger, Warsaw, IN (US); Peter Giannoudis, Leeds (GB); George J. Haidukewych, Orlando, FL (US); Daniel S. Horwitz, Salt Lake City, UT (US); Frank A. Liporace, Fort Lee, NJ (US); Andrew Sems, Oronoco, MN (US)

(73) Assignee: Biomet, C.V. (NL)

( * ) Notice: Subject to any disclaimer, the term of this patent is extended or adjusted under 35 U.S.C. 154(b) by 429 days.

(21) Appl. No.: 12/547,596

(22) Filed: Aug. 26, 2009

(65) Prior Publication Data
US 2011/0054550 A1    Mar. 3, 2011

(51) Int. Cl.
*A61B 17/56* (2006.01)
*A61B 17/58* (2006.01)
*A61F 2/30* (2006.01)

(52) U.S. Cl. ............. 606/62; 606/86 R; 606/97; 606/99; 606/104

(58) Field of Classification Search .............. 606/62–68, 606/86 R, 96–98, 99, 104
See application file for complete search history.

(56) References Cited

U.S. PATENT DOCUMENTS

| | | | |
|---|---|---|---|
| 3,704,707 A | 12/1972 | Halloran | |
| 4,911,153 A | 3/1990 | Border | |
| 5,178,621 A | 1/1993 | Cook et al. | |
| 5,334,192 A | 8/1994 | Behrens | |
| 5,346,496 A | 9/1994 | Pennig | |
| 5,403,321 A | 4/1995 | DiMarco | |
| 5,403,322 A | 4/1995 | Herzenberg et al. | |
| 5,620,449 A | 4/1997 | Faccioli et al. | |
| 5,665,086 A | 9/1997 | Itoman et al. | |

(Continued)

FOREIGN PATENT DOCUMENTS
EP    640318 A1    3/1995
(Continued)

OTHER PUBLICATIONS

International Search Report dated May 11, 2011; International Application No. PCT/US2010/046476.

(Continued)

*Primary Examiner* — Andrew Yang
(74) *Attorney, Agent, or Firm* — Harness, Dickey

(57) ABSTRACT

An instrument system is provided for positioning an internal fixation prosthesis and guiding a cannulated bone drill during a surgical, radioscopic procedure for the repair of a fractured bone of a patient. The instrument system includes a target wire, a handle formed from a radio translucent material having a target hole for guided passage of the target wire along a target axis. The target axis coincides with the intersection of a first plane and a second plane orthogonal to the first plane. The instrument system also includes a nose component attached to an end of the handle and removably connectable to the prosthesis. The nose component includes an alignment sight formed from a radio-opaque material. When the prosthesis is connected to the nose component and the target wire is positioned through the target hole along the target axis, the image of the guide wire may be radioscopically viewed along a first line of sight contained in the first plane to bisect the image of the alignment device, thereby providing a first visual reference to the user for directing the first guide wire into the desired portion of the bone while holding the prosthesis in a desired position relative to the bone.

6 Claims, 16 Drawing Sheets

U.S. PATENT DOCUMENTS

| | | |
|---|---|---|
| 6,027,506 A | 2/2000 | Faccioli et al. |
| 6,036,696 A | 3/2000 | Lambrecht et al. |
| 6,039,739 A | 3/2000 | Simon |
| 6,126,661 A | 10/2000 | Faccioli et al. |
| 6,183,477 B1 | 2/2001 | Pepper |
| 6,517,546 B2 | 2/2003 | Whittaker et al. |
| 6,736,819 B2 | 5/2004 | Tipirneni |
| 6,958,067 B2 | 10/2005 | Whittaker et al. |
| 7,175,633 B2 | 2/2007 | Roth et al. |
| 7,575,578 B2 | 8/2009 | Wetzler et al. |
| 7,591,823 B2 | 9/2009 | Tipirneni |
| 7,887,545 B2 | 2/2011 | Fernandez et al. |
| 7,901,410 B2 | 3/2011 | Bigdeli-Issazadeh et al. |
| 2002/0058949 A1 | 5/2002 | Iaia |
| 2003/0065391 A1 | 4/2003 | Re et al. |
| 2003/0212405 A1 | 11/2003 | Choi |
| 2003/0220651 A1 | 11/2003 | Pusnik et al. |
| 2004/0059329 A1 | 3/2004 | Zander |
| 2004/0082959 A1 | 4/2004 | Hayes et al. |
| 2005/0096656 A1 | 5/2005 | Behrens |
| 2006/0200160 A1 | 9/2006 | Border et al. |
| 2007/0083213 A1 | 4/2007 | Siravo et al. |
| 2008/0154264 A1 | 6/2008 | Wack et al. |
| 2008/0231331 A1 | 9/2008 | Balraj et al. |
| 2008/0255573 A1 | 10/2008 | Willett et al. |
| 2008/0269744 A1 | 10/2008 | Kay et al. |
| 2008/0281326 A1 | 11/2008 | Watanabe et al. |
| 2008/0281331 A1 | 11/2008 | Fritzinger et al. |
| 2009/0143784 A1 | 6/2009 | Petersen et al. |
| 2009/0216238 A1 | 8/2009 | Stark |
| 2009/0270860 A1 | 10/2009 | Bergin et al. |
| 2009/0299375 A1 | 12/2009 | Wack et al. |
| 2009/0306718 A1 | 12/2009 | Tipirneni et al. |
| 2009/0318926 A1 | 12/2009 | Christie |

FOREIGN PATENT DOCUMENTS

| | | |
|---|---|---|
| EP | 1273271 B1 | 8/2007 |
| EP | 1356777 B1 | 1/2008 |
| EP | 1992297 B1 | 7/2009 |
| WO | WO 03/063682 A2 | 8/2003 |
| WO | WO 2008/017501 A1 | 2/2008 |
| WO | WO 2009/052294 A1 | 4/2009 |
| WO | WO 2009/087214 A1 | 7/2009 |

OTHER PUBLICATIONS

U.S. Appl. No. 12/547,583, filed Aug. 26, 2009.
U.S. Appl. No. 12/547,608, filed Aug. 26, 2009.

METHOD FOR IMPLANTING A HIP FRACTURE NAIL SYSTEM

BACKGROUND

This disclosure relates in general to surgical devices and procedures, and more particularly, to internal fixation devices, the associated instrumentation and procedures for the repair of fractured bones.

Hip fracture nail (HFN) systems (also referred to as reconstruction nail systems) are currently available for surgically treating a wide range of proximal femoral fracture indications. HFN systems include an intramedullary nail that is sized and shaped for surgical implantation into the intramedullary canal of the fractured, proximal femur. The proximal portion of the nail has a smooth, transverse bore that retains a lag screw or the like having a distal end that anchors into the femoral head of the femur, such that the construct holds the femoral neck and the diaphysis (shaft) of the femur at a fixed angle with respect to each other, while allowing "sliding compression" of the fractured, proximal femur to promote proper healing. Typically this neck/shaft angle is in the range of 125 to 130 degrees. The proximal portion of the nail may also include another transverse, smooth bore that retains an anti-rotation screw alongside and proximal to the lag screw. Manufacturers typically provide HFN systems with both long and short versions of the nail and in various sizes to accommodate patient anatomy variations.

Surgeons usually implant the hip fracture nail and screws with the aid of an x-ray radioscope (fluoroscope) in order to verify proper reduction of the fracture and to properly position the nail and screws in the femur. It is especially important to insert the distal end of the lag and antirotation screws into the central portion of the femoral neck and head so as not to weaken the construct or to break out through the articulation surface of the femoral head. Therefore, manufacturers have provided special instrumentation for implanting the HFN system. Such instrumentation typically includes a target jig that attaches to the proximal end of the nail. The target jig provides a handle for holding and positioning the nail into the femur with the aid of radioscopic visualization. The target jig also includes target holes aligned with the lag screw and antirotation screw holes in the nail, to aid the surgeon in drilling the pilot holes into the femoral neck and head to receive the lag and anti-rotation screws. Portions of the target jig may be radiolucent in order to radioscopically visualize the nail, while other portions of the target jig may be radio opaque in order to provide visual references for aligning and positioning the nail inside the femur so that the axis of the lag screw passes approximately through the center of the femoral neck and head. Unfortunately during current standard HFN implantation procedures, it is usually necessary for the surgeon to take several radioscopic images in the lateral-medial and anterior-posterior directions in order to reduce the fracture and to properly position the nail in the femur. This is primarily because it is often difficult for the surgeon to discern if the radioscopic view is optimal for directing a guide wire through the femoral neck and to the proper depth in the femoral head. The guide wire is needed for guiding a cannulated drill to create a pilot hole for the lag screw. Clearly, each radioscopic image increases exposure of the surgeon, staff and patient to radiation and adds to the surgical procedure time and costs. What is needed, therefore, is improved instrumentation to aid the surgeon in properly implanting a hip fracture nail into the femur of a patient when the instrumentation is used in conjunction with a radioscopic imaging device.

Another challenge faced by orthopaedic surgeons is effectively managing a number of differently configured and sized IM nails and instruments that are provided by manufacturers due to the variation of patient anatomies. Currently available HFN systems include sets of IM nails in various sizes for each of a plurality of femoral neck/shaft angles. Each of these neck/shaft angle sets require a dedicated target jig, so it is necessary to match the correct IM nail with the correct target jig when attaching the IM nail to the target jig during the surgical procedure. Obviously, mismatching the IM nail and target jig may extend the duration of the procedure and cause unnecessary contamination of sterile components, resulting in higher surgical costs. What is also needed, therefore, is an improved HFN system to reduce confusion during the surgical procedure related to matching each of the angular versions of the IM nail to its dedicated target jig.

BRIEF DESCRIPTION OF DRAWINGS

While this specification concludes with claims that particularly point out and distinctly claim the invention, the following description and the accompanying drawings further illustrate some non-limiting examples of the claimed invention. Unless otherwise indicated, like reference numerals identify the same elements.

DETAILED DESCRIPTION

In this disclosure, the terms "anterior, posterior, lateral and medial" generally refer to the front, back, outside and midline of the surgical patient, respectively, although these terms are also used in reference to the devices. Also, it should be noted that the term "user" may refer to a surgeon or any one of a number of individuals who assist the surgeon during the bone fracture repair procedure.

Figure 1:
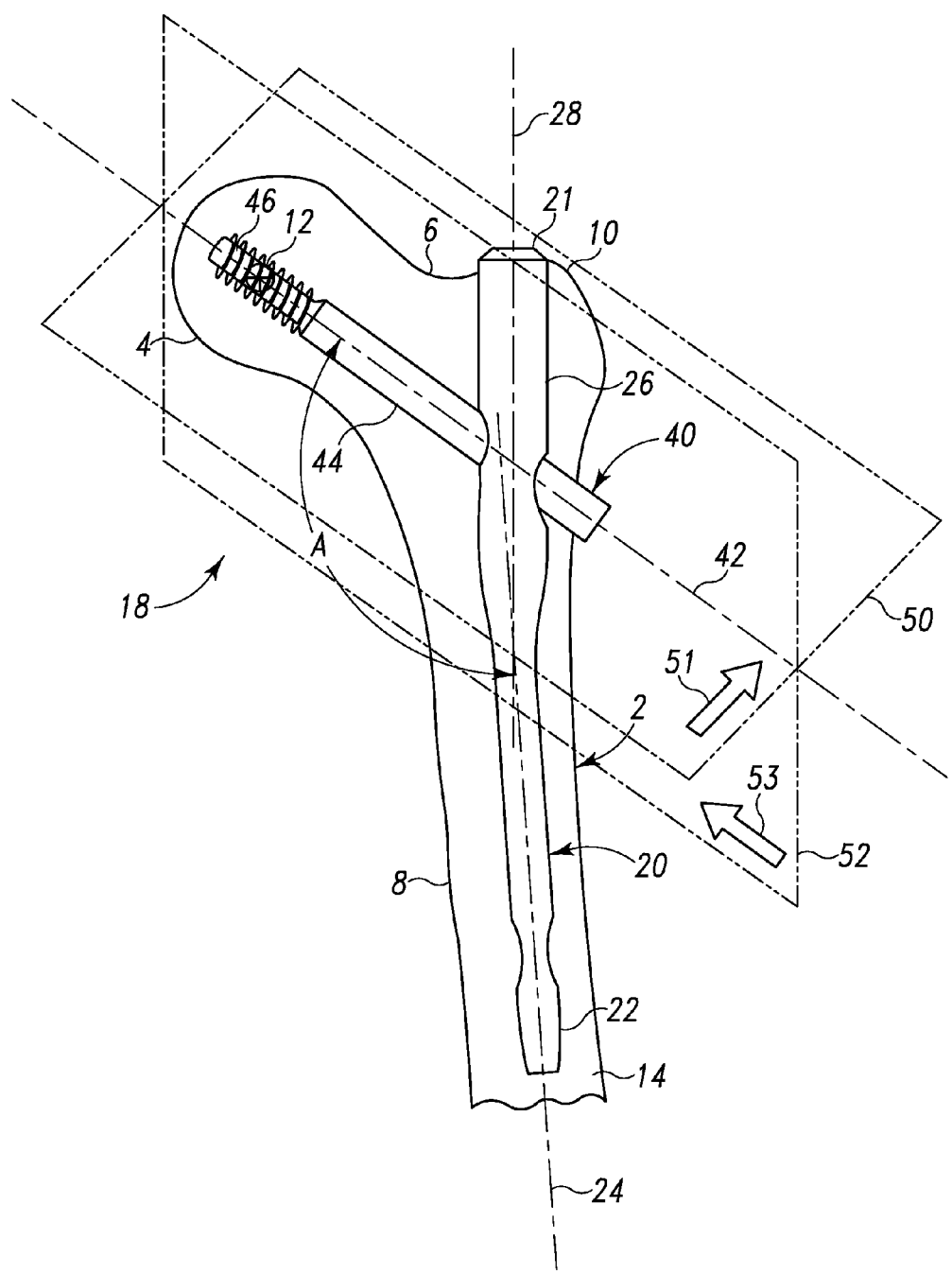
FIG. 1 is an anterior-lateral view of a hip fracture nail (HFN) assembly, which includes an intramedullary (IM) nail and a lag screw defining a lag screw axis, implanted into a proximal femur of a patient.

FIG. 1 is an anterior-lateral view of a hip fracture nail prosthesis 18 (or HFN prosthesis 18) implanted into the proximal portion of a femur 2 having a femoral head 4 with a center 12, a femoral neck 6, a trochanter 10, an intramedullary canal 14 and a femoral diaphysis 8. HFN prosthesis 18 includes an intramedullary nail 20 (or IM nail 20) and a lag screw 40. IM nail 20 includes a proximal shaft portion 26 defining a proximal shaft axis 28 and a distal shaft portion 22 defining a distal shaft axis 24 that may be slightly inclined relative to proximal shaft axis 28 to conform to the shape of femur 2. Lag screw 40 defines a lag screw axis 42 and includes a proximal barrel portion 44 and a distal threaded portion 46. Proximal portion 26 may slidingly retain barrel portion 40 of lag screw 40. Lag screw axis 42 and distal shaft portion axis 24 define a femoral neck-diaphysis angle indicated by the letter A, which corresponds approximately to the angle formed between the femoral neck 6 and the femur diaphysis 8. For most patients, this angle is approximately in the range of 125-130 degrees.

Distal threaded portion 46 is designed for threadable engagement into the bone in the center portion of the femoral head. However, there are different but functionally equivalent devices for anchoring into the femoral neck and head, including "blade" types of lagging devices for use with femoral nails, and reference to distal threaded portion 46 of lag screw 40 is not intended to be limiting.

HFN prosthesis may also include an end cap 21 and a retaining screw (hidden) inside of the internally threaded, proximal portion 26 of IM nail 20 for retaining lag screw 40. All of the components of HFN prosthesis 18 may be formed from any one or more of a number of biocompatible, radio-opaque materials, including a titanium alloy and stainless steel, as is well known in the art.

FIG. 1 also shows an anterior-posterior plane 50 (or AP plane 50 or first plane 50) that is orthogonal to a lateral-medial plane 52 (or LM plane or second plane 52). The intersection of AP plane 50 and LM plane 52 coincides with lag screw axis 42. A first line of sight 51 is contained in AP plane 50. A second line of sight 53 is contained in LM plane 52. As will be described, the first line of sight 51 and the second line of sight 53 generally correspond to the optimal set-up directions of a radioscopic imaging device when positioning IM nail 20 in femur 2 in order to direct a targeting guide wire along lag screw axis 42 and through center 12 of femoral head 4. Once properly inserted into femoral neck 6 and femoral head 4, this targeting guide wire may be used safely to guide a cannulated drill to create a pilot hole for lag screw 40, as is well known in the art.

The actual direction of the first line of sight 51 within the AP plane 52 with respect to lag screw axis 42 may vary, depending on the skill level of the user. Optimally, however, the first line of sight 51 is approximately perpendicular to lag screw axis 42 and within AP plane 52. As will be described, this is especially significant when inserting a guide wire into femoral head 4 to the desired depth to prevent penetration of the guide wire tip through the articulation surface of femoral head 4. Similarly, the actual direction of the second line of sight 53 within the LM plane 52 with respect to distal shaft axis 24 may vary, depending again on the skill level of the user. In this case, the optimal direction of the first line of sight 51 is approximately parallel to lag screw axis 42 and within LM plane 52. As will be described, particular features of the devices disclosed herein assist the user in radioscopically visualizing IM nail 20 along the first and second lines of sight in order to properly set the insertion depth and the version angle of IM nail 20 in femur 2.

HFN prosthesis 18 may also include an anti-rotation screw (not shown) as noted previously. The present disclosure, however, is directed primarily to devices and procedures associated with the proper positioning of IM nail 20 and lag screw 40 into femur 2, since the positioning of the anti-rotation screw into femur 2 is predetermined by the prior positioning of lag screw 40 into femur 2. HFN prosthesis 18 may also include additional screws and other internal components not described herein. Additional description of an exemplary device that is generally similar to HFN prosthesis 18 and that includes an anti-rotation screw may be found in U.S. Pat. App. No. 2006/0106386A1 entitled "Orthopaedic Screw and Method" filed by E. Reber, et al, on Jun. 28, 2005.

Figure 2:
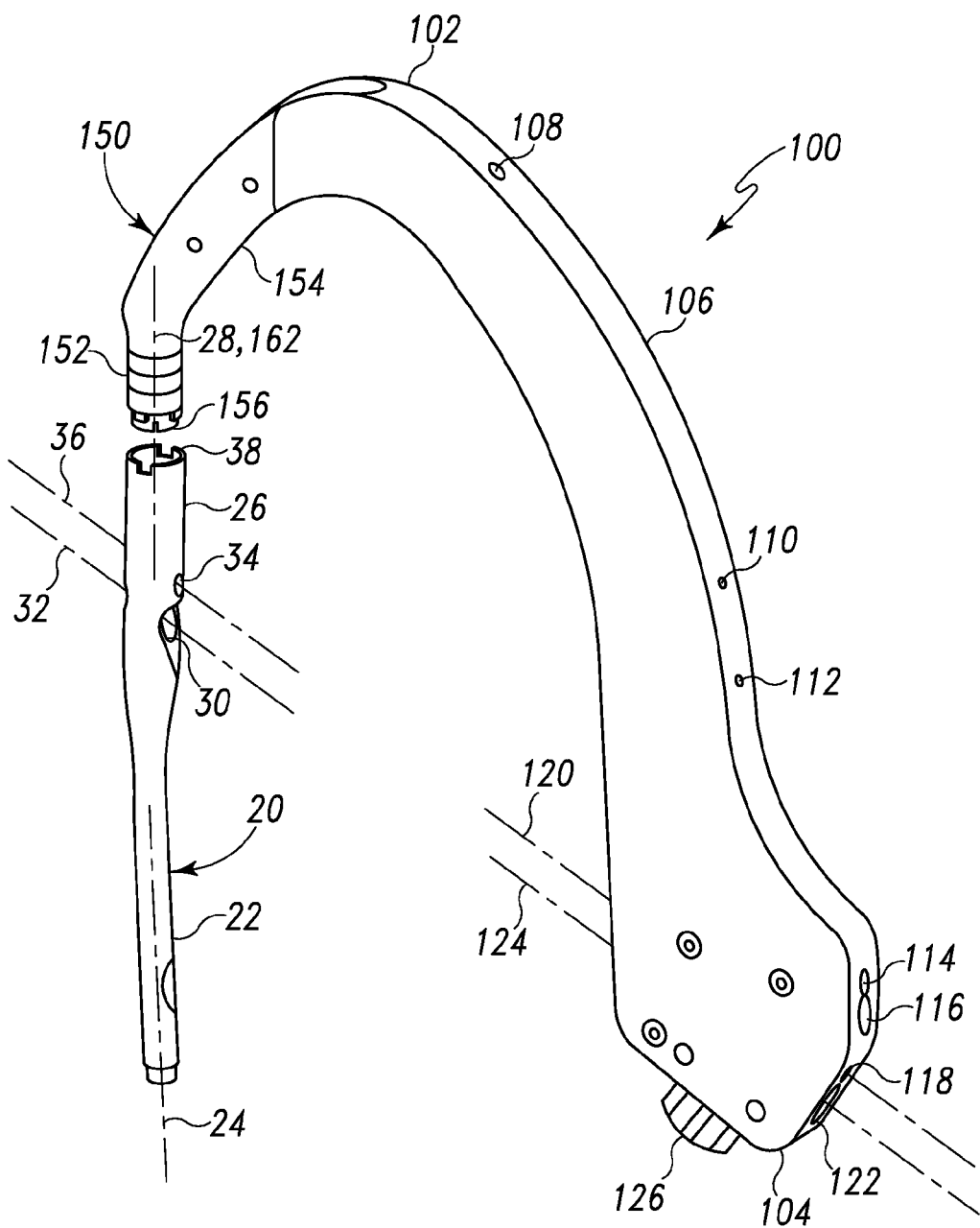
FIG. 2 is a perspective view of a target jig having a nose component, which is shown in connecting alignment with the IM nail of FIG. 1.

FIG. 2 is a perspective view of a target jig 100 shown in connecting alignment with IM nail 20. Target jig 100 releasably attaches to IM nail 20 to aid the user in positioning IM nail 20 in femur 2, to attach stabilizing guide wires, and to drill pilot holes into femur 2 to receive lag screw 40, as well as the other screws noted previously. Target jig 100 may include an arcuate-shaped handle 106 having a superior end 102 and an inferior end 104. Handle 106 may be formed from a radio-translucent, biocompatible material such as carbon-filled PEEK. A nose component 150 connects to superior end 102 of handle 106. Nose component 150 includes a yoke portion 154 and a shaft portion 152 that extends distally from superior end 102 of handle 106 to define a nose axis 162. Nose axis 162 is coaxial with proximal shaft axis 28 of IM nail 20 when IM nail 20 is attached to target jig 100. Nose component 150 may be formed from a biocompatible, radio-opaque material such as a titanium alloy or a stainless steel. Nose component 150 also includes a nose connector 156 and IM nail 20 includes nail connector 38 for releasably attaching nose component 150 to IM nail 20.

Figure 5A:
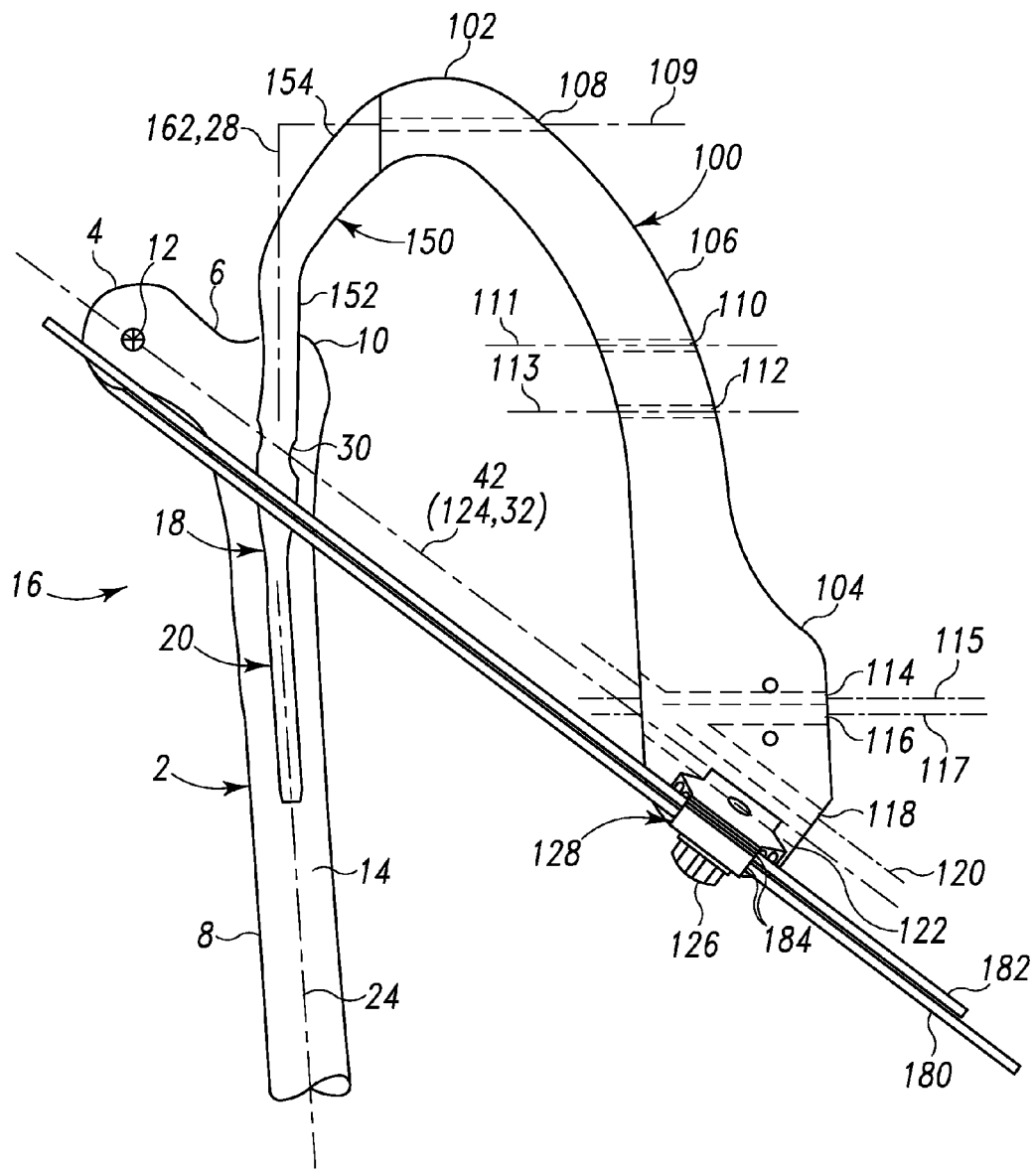
FIG. 5A is an anterior view, as may be radioscopically imaged, of the target jig connected to the IM nail, which has been positioned at an initial insertion depth in the proximal femur, and showing a tower extension assembly that includes a tower containing two, parallel guide wires attached to the target jig.
Figure 6:
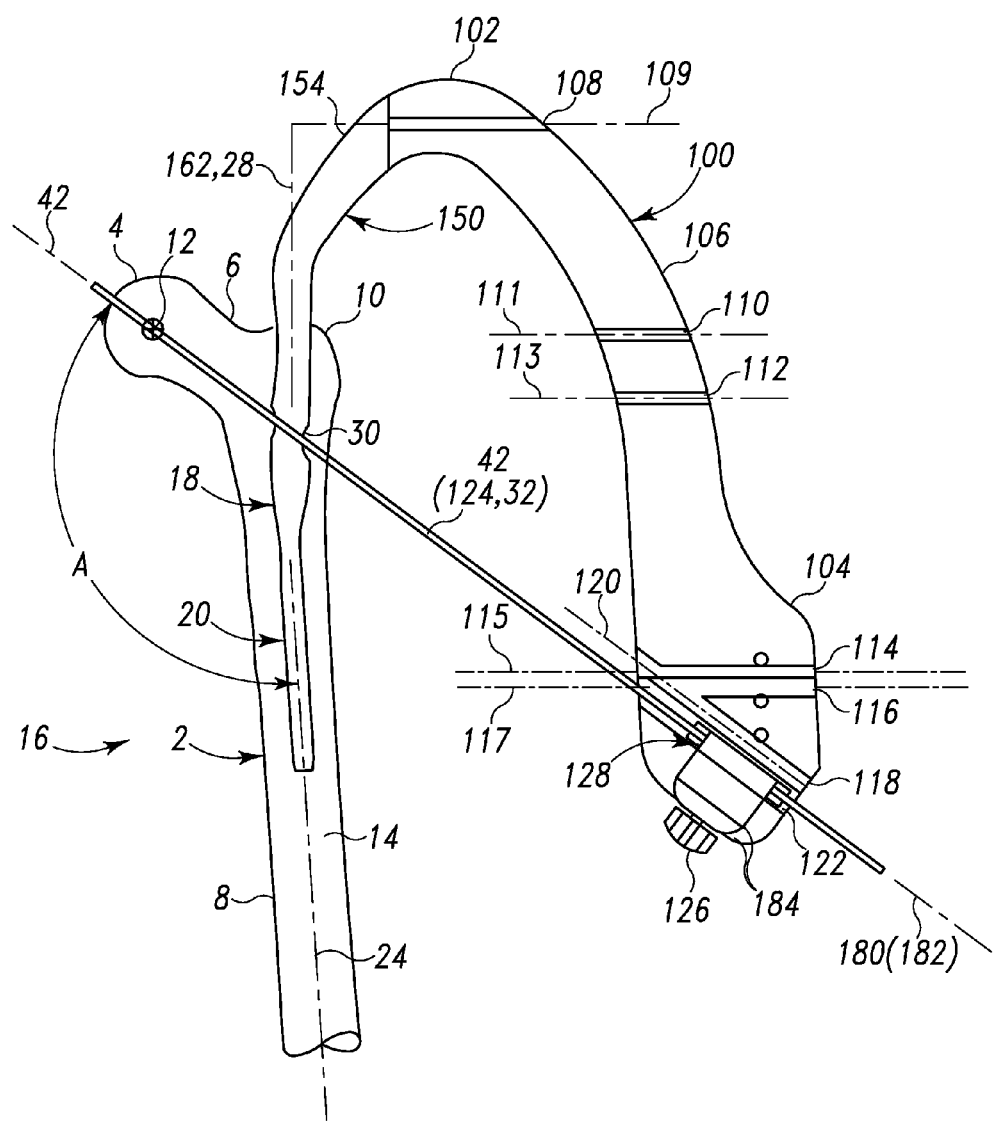
FIG. 6 is a view of the IM nail and the tower extension assembly shown in FIG. 5A, as may be radioscopically imaged along a second line of sight contained in an anterior-posterior plane of the target jig while the IM nail is in a desired insertion depth in the proximal femur, such that the lag screw axis appears to pass through the center of the femoral head.

As shown in FIG. 2, FIG. 5A and FIG. 6, handle 106 of target jig 100 may include a first wire hole 108 defining a first target axis 109, a second wire hole 110 defining a second wire axis 111, a third wire hole 112 defining a third wire axis 113, a first target hole 114 defining a first target axis 115, a second target hole 116 defining a second target axis 117, an antirotation target hole 118 (or AR target hole 118) defining an AR target axis 120 and a lag target hole 122 defining a lag target axis 124. A clamp element 126 assembles to inferior end 104 of handle 106 and is shown in greater detail in FIG. 8.

FIG. 2 also shows IM nail 20 to include a lag screw hole 30 defining a lag screw hole axis 32 and an AR hole 34 for receiving an AR screw (not shown) and defining an AR hole axis 36, which is parallel to lag screw hole axis 32. As shown in FIG. 5 and FIG. 6, when IM nail 20 is attached to target jig 100, lag screw hole axis 32 and lag target axis 124 align to form a lag screw axis 42. As will be described, a user may attach target jig 100 to IM nail 20 and manipulate IM nail 20 in femur 2, such that lag screw axis 42 passes approximately through center 12 of femoral head 4 prior to drilling the pilot hole for lag screw 40.

Figure 3:
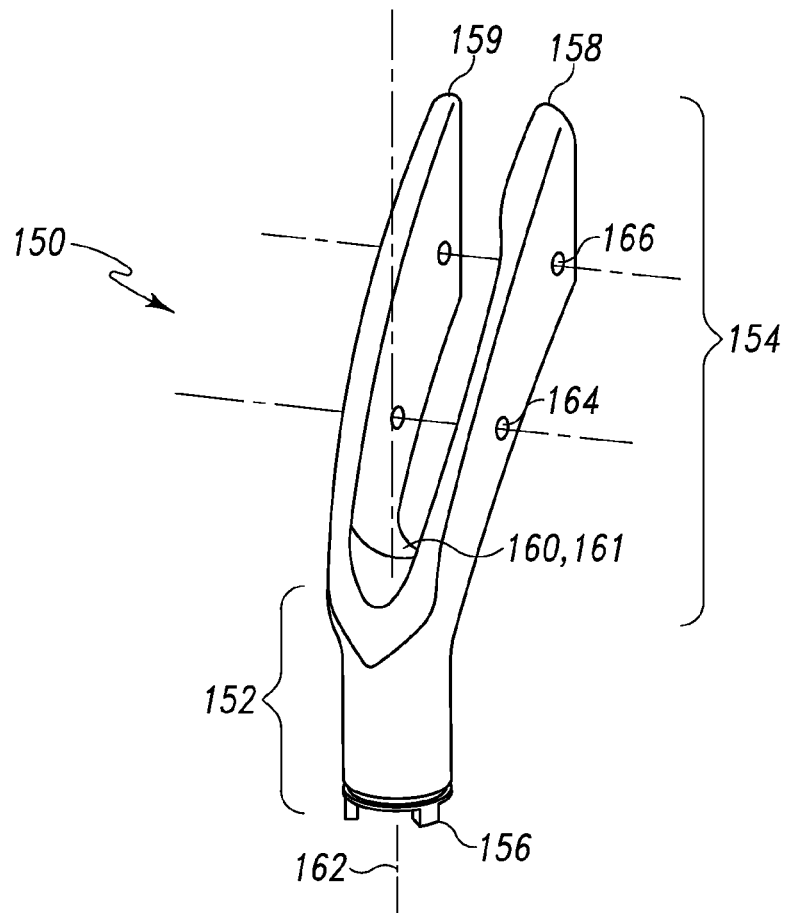
FIG. 3 is a detailed, perspective view of the nose component of FIG. 2.
Figure 4:
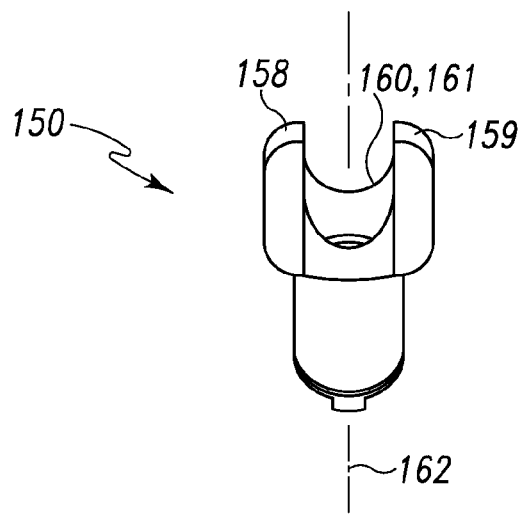
FIG. 4 is a front view of the nose component of FIG. 3, showing the nose component with an alignment sight having a pair of spaced-apart, opposing arms that form a U-shaped gap.

FIG. 3 is a detailed, perspective view and FIG. 4 is a front view (corresponding to the lateral-medial view when target jig 100 is used to position IM nail 20 in femur 2) of nose component 150 of target jig 100, showing a yoke portion 154 and a shaft portion 152. Yoke portion 154 has a left arm 158 and an opposing right arm 159, together forming an alignment sight 160 defining a U-shaped gap 161 that centers on shaft portion axis 162 when viewed as shown in FIG. 4. Since nose component 150 is formed from a radio-opaque material, alignment sight 160 is visible on a radioscopic image. Nose component 150 also has first and second attachment holes, 164 and 166, for attachment of nose component 150 to handle 106 with pin fasteners. Target jig 100 may be adapted for single use disposability or for repeated sterilizations using conventional techniques to allow usage for multiple surgical procedures.

FIG. 5A and FIG. 6 are views of a hip fracture nail (HFN) system 16 that includes target jig 100, HFN prosthesis 18 and a tower extension assembly 128. HFN system 16 may also include a target tube assembly 60, shown in FIG. 7. The surgical steps required to reach the point of the surgical repair procedure depicted in these views, including wound site preparation, initial reduction of the fractured bone and reaming of the IM canal of femur 2, are well-known in the art and are described in the earlier referenced patent application to Reber, et al.

FIGS. 5A, 6, 7, 9, 10 11 and 12 generally depict the steps that a user may follow to use target jig 100, in conjunction with additional elements to be described, to position IM nail 20 in femur 2 and to drill a pilot hole for lag screw 40 to the proper depth, such that lag screw axis 42 passes approximately through center 12 of femoral head 4. It should be noted that the user may desire to position lag screw axis 42 slightly inferior to center 12, if the user desires to also insert an AR screw proximal to and alongside of lag screw 40. What is important is that lag screw 40 (and the AR screw, if used) is inserted into the central, cancellous bone of the femoral neck 6 and femoral head 4, such that it does not penetrate the articulation surface of femoral head 4 and also is not likely to cause a new head and/or neck fracture when bearing load during the post-operative period of bone healing.

FIG. 5A is an anterior view, as may be imaged by a radioscopic (X-ray fluoroscopic, etc.) imaging device, of HFN system 16, showing IM nail 20 positioned within intramedullary canal 14 of femur 2 at an initial insertion depth. Lag target hole 118 appears to align through center 12 of femoral head 4, but this may be misleading since this view is not along the first line of sight 51 (FIG. 1). In order to properly visualize the alignment of lag target hole 118 with lag screw hole 30 and center 12 of femoral head 4, the user may redirect the radioscopic imaging device to obtain a view approximately along the first line of sight 51 within the anterior-posterior plane 52 (FIG. 1).

Figure 5B:
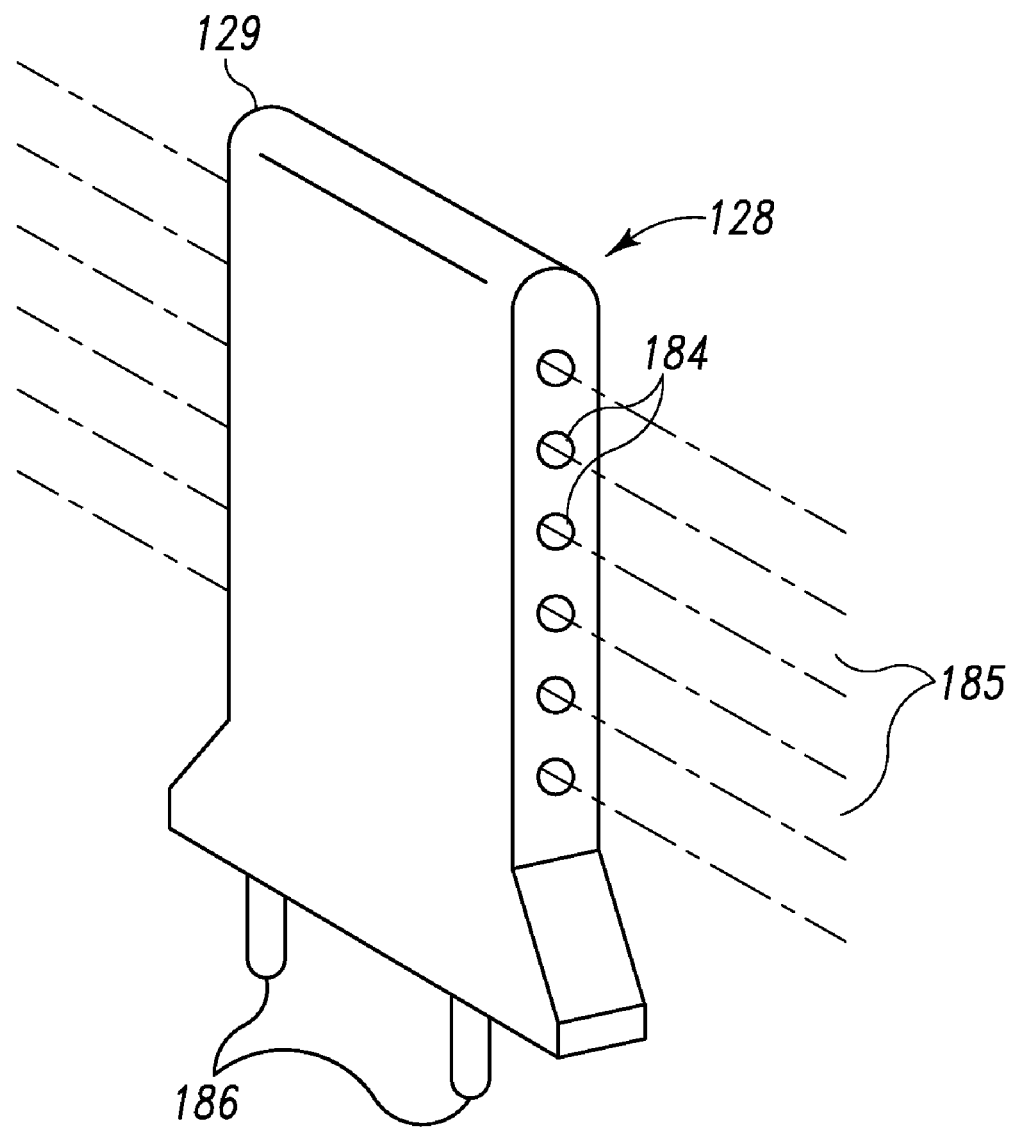
FIG. 5B is a perspective view of the tower shown in FIG. 5A.
Figure 8:
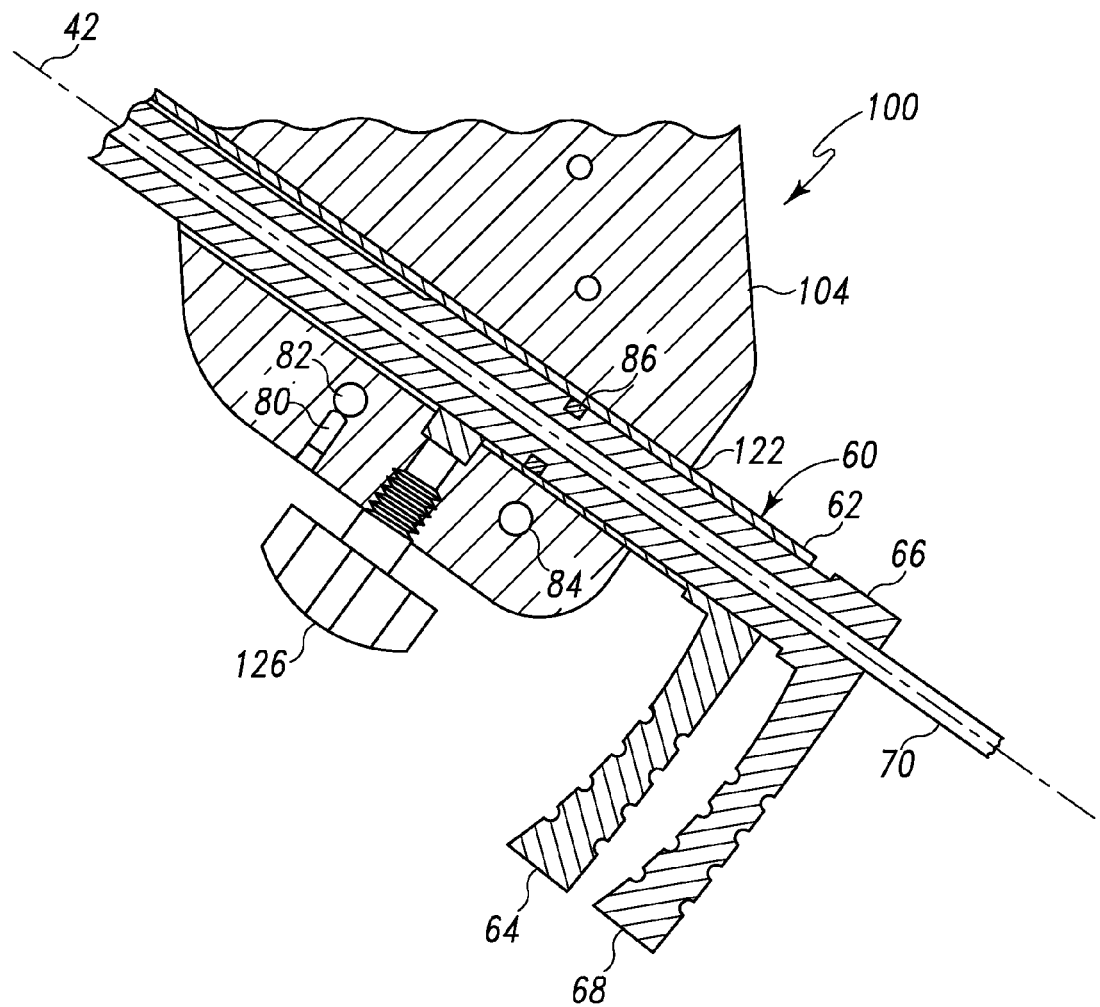
FIG. 8 is a detailed, sectional view of a portion of the target tube assembly and the target jig shown in FIG. 7.

As shown in FIG. 5A and FIG. 5B, tower extension assembly 128 removably attaches to either side (to repair a hip fracture on either side of a patient) of inferior end 104 of handle 106. Tower extension assembly 128 includes a tower 129 that may be formed, for example, from a thick, rectangular, metal plate. A pair of spaced apart posts 186 extend from one end of tower 129 for removable insertion into a first tower hole 82 and second tower hole 84 (FIG. 8). A spring detent 80 (FIG. 8) mounted into handle 106 holds either one of the pair of posts 186 with a predetermined force to secure tower 129 to handle 106 during use, yet still allowing easy insertion and removal. Tower 128 further includes a plurality of spaced-apart, parallel, through-holes or channels 184 that define a like plurality of parallel, channel axes 185. Each of channels 184 extend transversely across the entire width of tower 128, is offset from lag target hole axis 124 and are sized to guide one of a pair of identical, conventional, metal guide wires, herein referred to as a first alignment wire 180 and a second alignment wire 182.

Tower extension assembly 128 provides a first visual reference to the user for adjusting the position of IM nail 20 to the desired insertion depth so that lag screw axis 42 passes through center 12 of femoral head 4. The user inserts first alignment wire 180 into one of channels 184 of tower 128 and second alignment wire 182 into another of channels 184, such that they pass over the outside of the patient's upper leg. The selection of which of channels 184 to use depends primarily on the overall thickness of soft tissue layers overlying femur 2. For obese patients, the user may select the outermost of channels 184 with the greatest offset from lag target hole axis 124. First alignment wire 180 and second alignment wire 182 may then be extended past femoral head 4 as shown in FIG. 5A and radioscopically imaged in the general anterior-posterior direction. Target jig 100 may then be used to manipulate IM nail 20 and adjust the insertion depth. In addition, the user may adjust the aim of the radioscopic imaging device and take additional radioscopic images until a view similar to the view of FIG. 6 is obtained. Obviously, the number of radioscopic images required to obtain the view of FIG. 6 will vary largely on the skill of the user, among other factors. However, using tower extension assembly 128 is expected to decrease the number of radioscopic images that most users will require to position IM nail 20 at the desired insertion depth in femur 2.

FIG. 6 is a view of HFN system 16, as may be radioscopically imaged along the second line of sight 51 (FIG. 1) contained in AP plane 50 when IM nail 20 is positioned at a desired insertion depth in the proximal femur, such that lag screw axis 42 aligns through center 12 of femoral head 4. As shown in FIG. 6, first alignment wire 180 obstructs the view of second alignment wire 182, thereby providing a first visual reference that the radioscopic imaging device is directed along the first line of sight 51. First alignment wire 180 also appears to pass through center 12 of femoral head 4, indicating proper alignment of lag screw axis 42 with center 12 of femoral head 4. However, lag screw axis 42 may not necessarily pass through center 12 until a similar procedure is also completed for the medial-lateral (LM) direction, as will be described for FIGS. 9 and 10.

Figure 7:
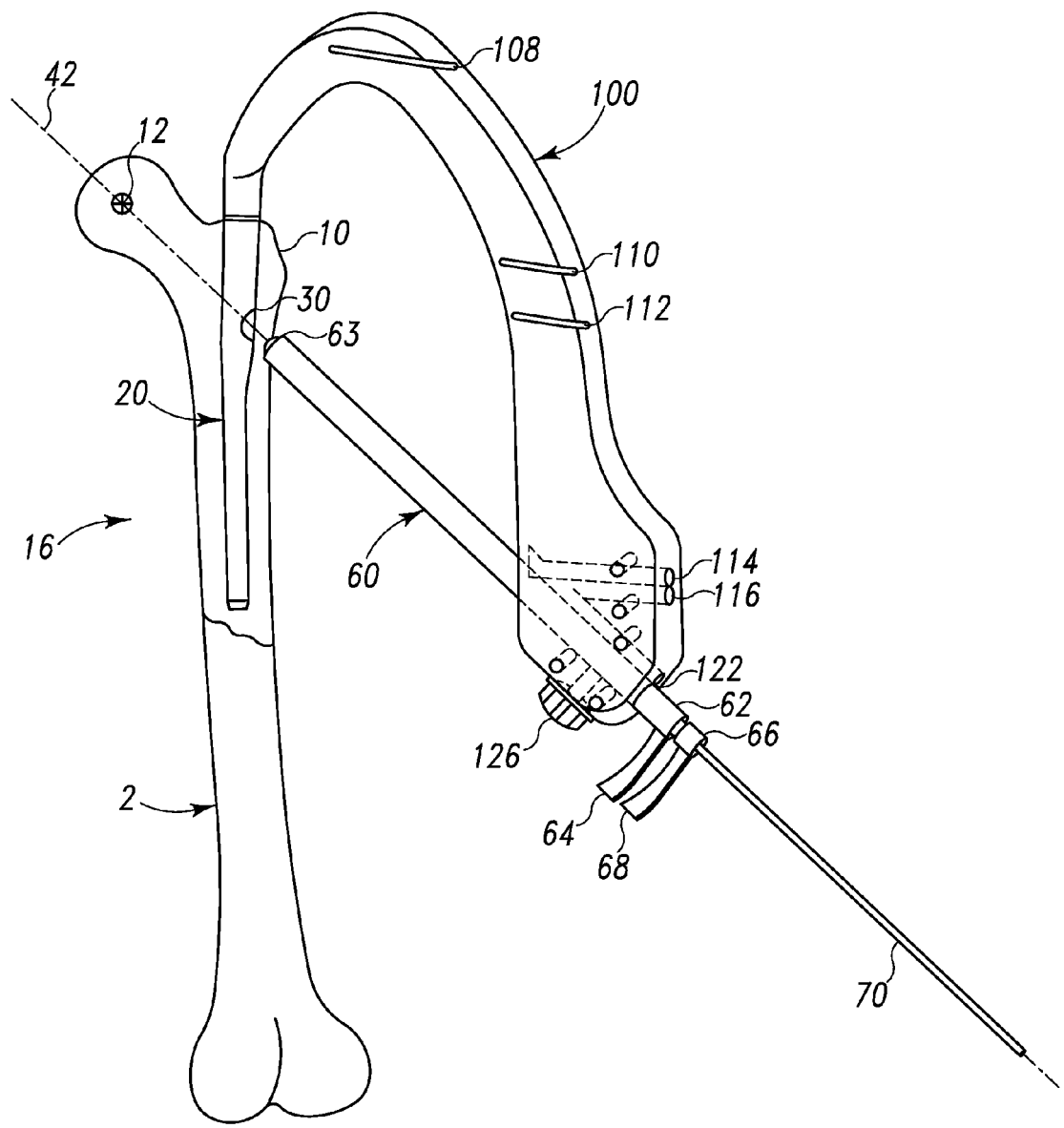
FIG. 7 is an anterior view of the target jig and the IM nail initially positioned as shown in FIG. 5A, and also showing a target tube assembly inserted into the target jig along the lag screw axis.

FIG. 7 is an anterior view of target jig 100 and IM nail 20 positioned in femur 2. In this view, lag screw axis 42 is already aligned in the AP direction, as just described for FIG. 6. The user (with assistance) has removed tower extension assembly 128 and has assembled target tube assembly 60 into lag target hole 122 of target jig 100 while holding target jig 100 in position in femur 2. If desired, the user may pass a guide wire (not shown) through third wire hole 112 and drill the guide wire into the near cortex of femur 2 to temporarily hold the position of IM nail 20 in the bone. The second wire hole 110 aligns with the proximal end of IM nail 20. The user may insert a guide wire into hole 110 to help ascertain the position of the proximal end of IM nail 20 relative to the superior surface of trochanter 10.

FIG. 8 is a detailed, sectional view of a portion of target tube assembly 60 and target jig 100. Target tube assembly 60 includes an outer tube 62 and an inner tube 66. Referring now to both FIG. 7 and FIG. 8, outer tube 62 fits slidably through lag target hole 122. Outer tube 62 has a distal end 63 that the user may position against the near surface of femur 2, and a proximal handle 64 for inserting, positioning and removing outer tube 62. The user may lock the axial position of outer tube 62 by tightening clamp 126. Inner tube 66 fits slidably into the inside of outer tube 62. A friction ring 86 provides a localized, tight fit between outer tube 62 and inner tube 66 in order to prevent inner tube 66 from sliding out of outer tube 62 inadvertently. The inside diameter of inner tube 66 is sized to guide a lag target wire 70 along lag screw axis 42. Inner tube 66 also includes a proximal handle 68. Each of outer tube 62 and inner tube 64 may be formed from a metal such as stainless steel and may be easily cleaned and sterilized for reuse.

With lag screw axis 42 approximately aligned with center 12 of femoral head 4 as viewed in the anterior-posterior direction, and with target tube assembly 60 assembled into target jig 100 as shown in FIG. 7, the user may next position IM nail 20 to a desired version angle about the long axis of femur 2, such that lag screw axis 42 passes through center 12 of femoral head 4 as viewed in the medial-lateral direction. This is also known in the art as "setting the version" of IM nail 20 and is described next.

Figure 9:
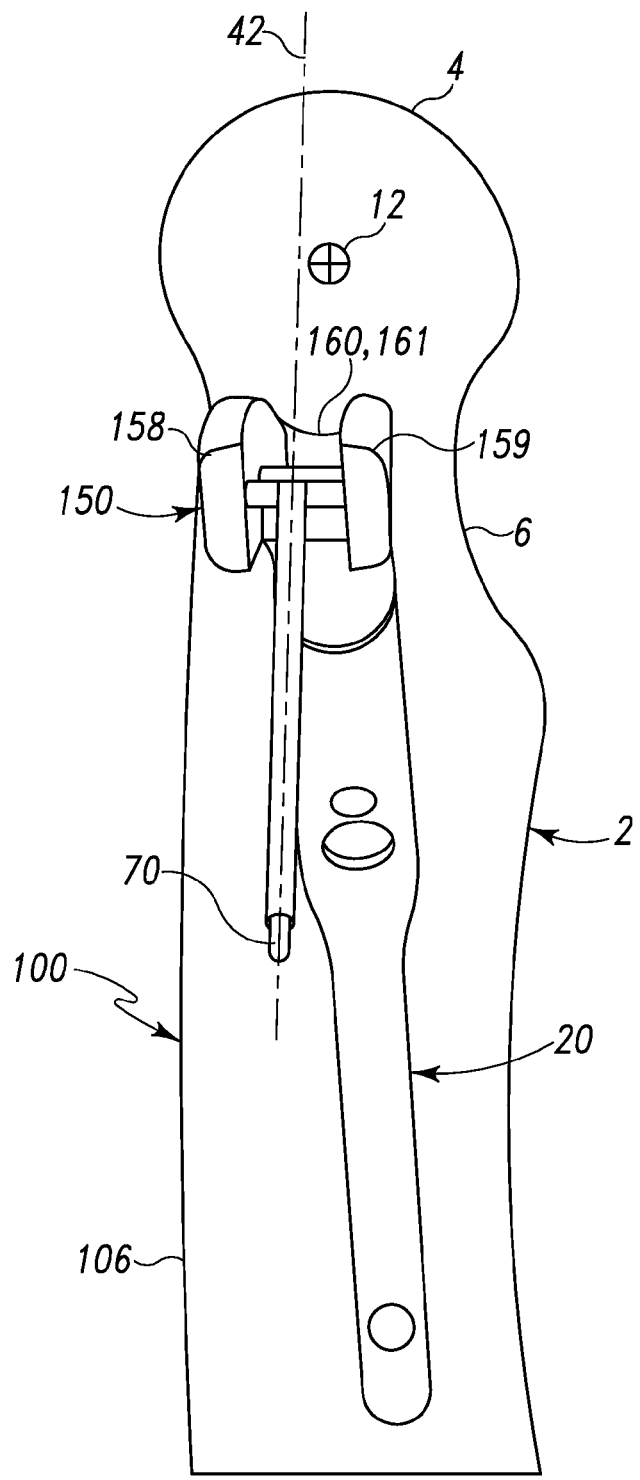
FIG. 9 is a lateral view of the target jig and the IM nail, as may be radioscopically imaged, positioned at the desired insertion depth as shown in FIG. 6, but positioned at an initial version angle in the proximal femur of the patient, and showing only a portion of the U-shape gap.
Figure 10:
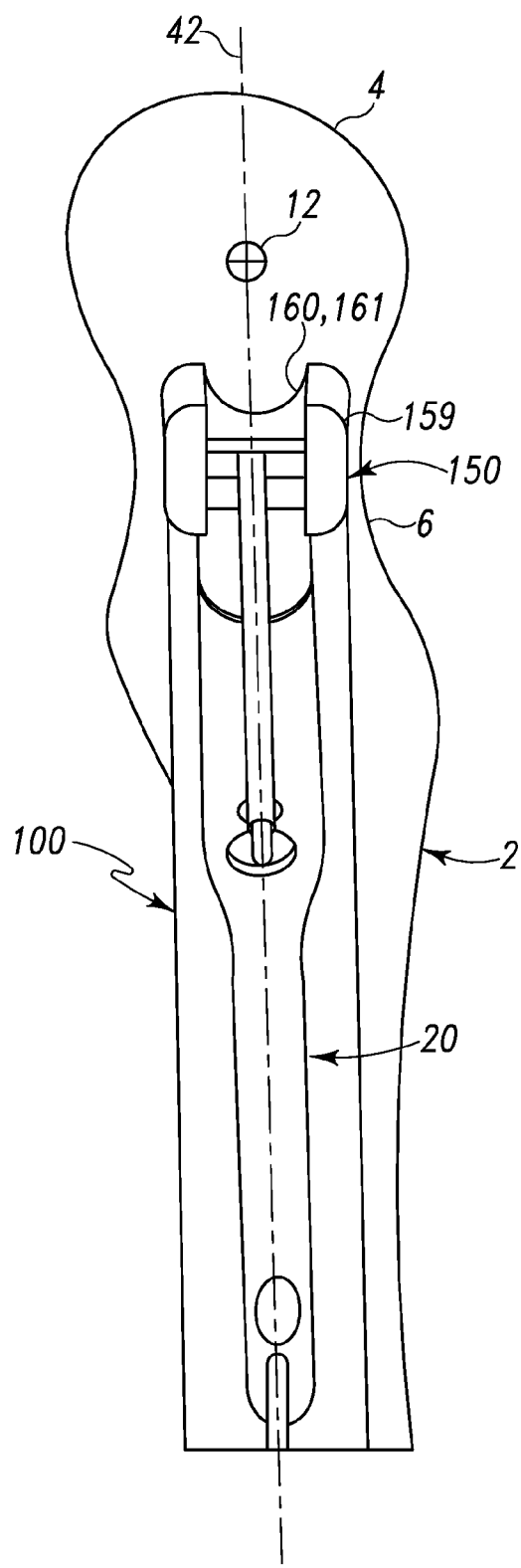
FIG. 10 is a view of the target jig and the IM nail positioned at a desired version angle, as may be radioscopically imaged, along a first line of sight contained in a lateral-medial plane, such that a target wire inserted in the target jig along the lag screw axis is directed approximately through the center of the femoral head and centered on the U-shaped gap of the alignment sight.
Figure 11:
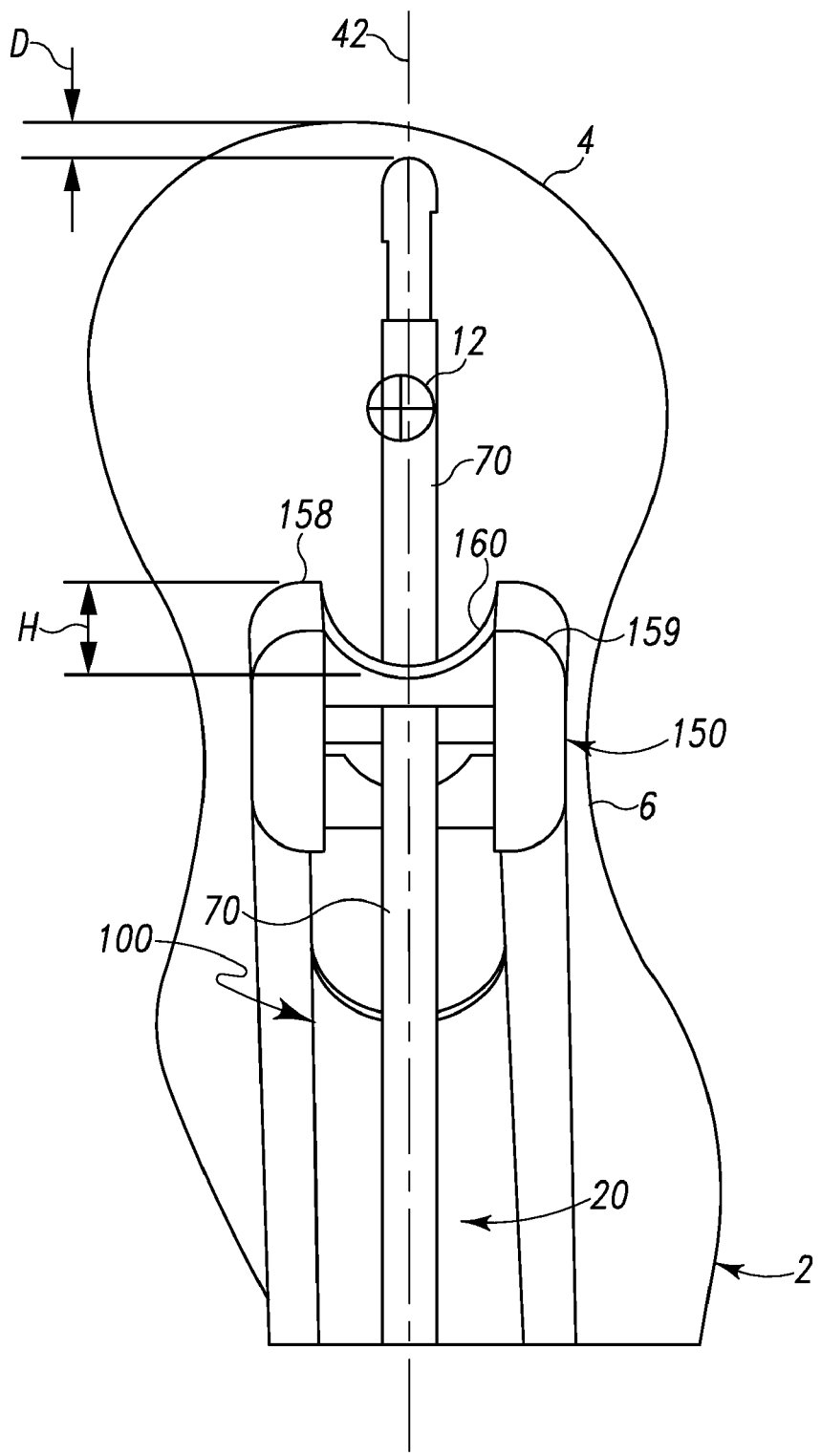
FIG. 11 is the same view as shown in FIG. 10, but now also showing the target wire advanced into the femoral head to a desired penetration depth.

FIG. 9 is lateral view of target jig 100 (showing only part of handle 106) and IM nail 20, as they may be initially positioned in femur 2 of the patient and radioscopically imaged. Nose component 150, IM nail 20 and lag target wire 70 are radio-opaque and are clearly visible, even though partially obstructed by translucent handle 106 of target jig 100. Left arm 158 and opposing right arm 159 of alignment sight 160 of nose component 150 together form U-shaped gap 161. As shown in FIG. 9, a portion of alignment sight 160 is obstructed by right arm 159, thereby providing a second visual reference to the user regarding alignment of lag screw axis 42 through center 12 of femoral head 4. Based on the view shown in FIG. 9, the user may turn target jig 100 slightly about the long axis of femur 2 so that alignment sight 160 is centered directly beneath center 12 of femoral head 4, as shown in FIG. 10. This also aligns lag screw axis 42 with center 12 so that lag target wire 70 may be advanced into femoral head 4 as shown in FIG. 11. Nose component 150 is configured such that when the height of alignment sight 160 (indicated by the letter H in FIG. 11) appears on the x-ray image to be greatest, as shown in FIG. 11, the user knows that the distance of the tip of lag target wire 70 from the surface of femoral head 4 (indicated by the letter D in FIG. 11) is approximately the actual distance. This may also be confirmed by another radioscopic view in the anterior-posterior direction. Using alignment sight 160 in this way in combination with lag target wire 70, the user may safely advance lag target wire 70 into femoral head 4 without penetrating the articulation surface.

Figure 12:
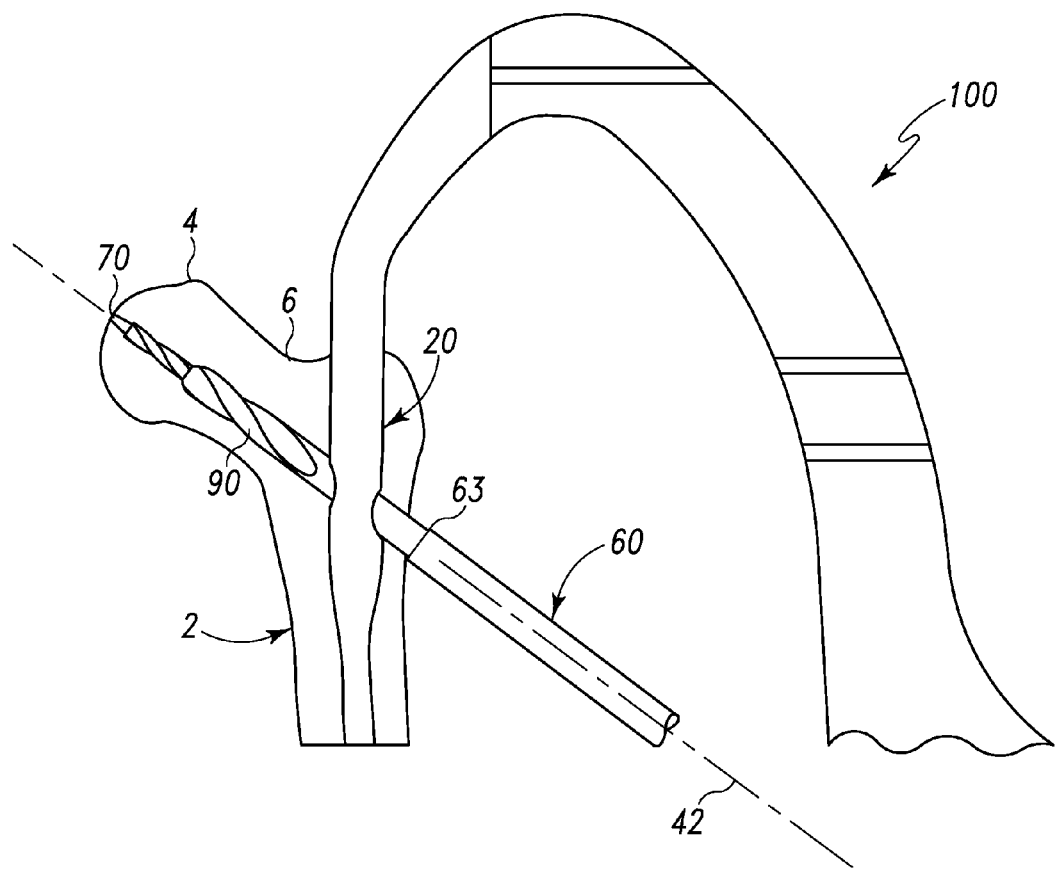
FIG. 12 is an anterior view of the target jig being used to guide a cannulated drill over the inserted target wire and into the femoral head to create a pilot hole for the lag screw shown in FIG. 1.

Once the user has inserted lag target wire 70 through femoral neck 6 to the desired depth into femoral head 4, the user may remove target tube assembly 60. The user may then use target jig 100, as shown in FIG. 12, to guide a cannulated drill 90 over lag target wire 70 and into femoral head 4 to create a pilot hole for lag screw 40 (shown in FIG. 1). Then the user may insert lag screw 40 (which is also cannulated) and remove lag target wire 70. At this stage of the procedure, IM nail 20 and lag screw 40 are properly positioned in femur 2 as shown in FIG. 1.

As described previously for FIG. 5, target jig 100 includes first wire hole 108 in the superior portion of handle 106. Prior to advancing lag target wire 70 into femoral head 4, the user optionally may insert a guide wire into first wire hole 108 and extend the wire over nose component 150 and femoral head 4 (without extending into the patient's tissue). The user may then observe the position of this guide wire, in combination with the methods already described for FIGS. 9 and 10, to aid in setting the version of IM nail 20 in femur 2.

Once the user has inserted lag screw 40 and "staked" IM nail 20 at the desired position in femur 2, the user may then insert the remaining screws and nail components and complete the implantation procedure. First target hole 114 and second target hole 116 of target jig 100 may be used to guide a drill and to insert locking screws in the distal shaft portion of IM nail 20. AR target hole may be used to guide a drill and to insert the AR screw, if provided. Internal components (not shown) of IM nail 20 may be assembled into the proximal portion of IM nail 20 to secure lag screw 40 (and the AR screw, if provided) and an end cap 21 (FIG. 1) may be attached to the proximal end of IM nail 20.

Although the previous description refers to observing the first visual reference for the AP plane first and the second visual reference for the LM plane second when positioning IM nail 20 in femur 2, it is also possible to do the reverse, that is, observe the second visual reference first and observe the first visual reference second. It is expected that most users will continue to move the radioscopic imaging device back and forth between the AP and LM views as they currently do using conventional nail systems. However, using the HFN system 16 and the methods described herein are expected to significantly reduce the number of times that users will need to move the imaging device and the number of radioscopic images taken during each procedure.

As described previously, various sizes and configurations of femoral, intramedullary nails are currently available to because of the variety of patient anatomies. In particular, the angle between the femoral neck and the femoral diaphysis (or neck-diaphysis angle) typically varies between about 125 to 130 degrees for most patients.

Figure 13A:
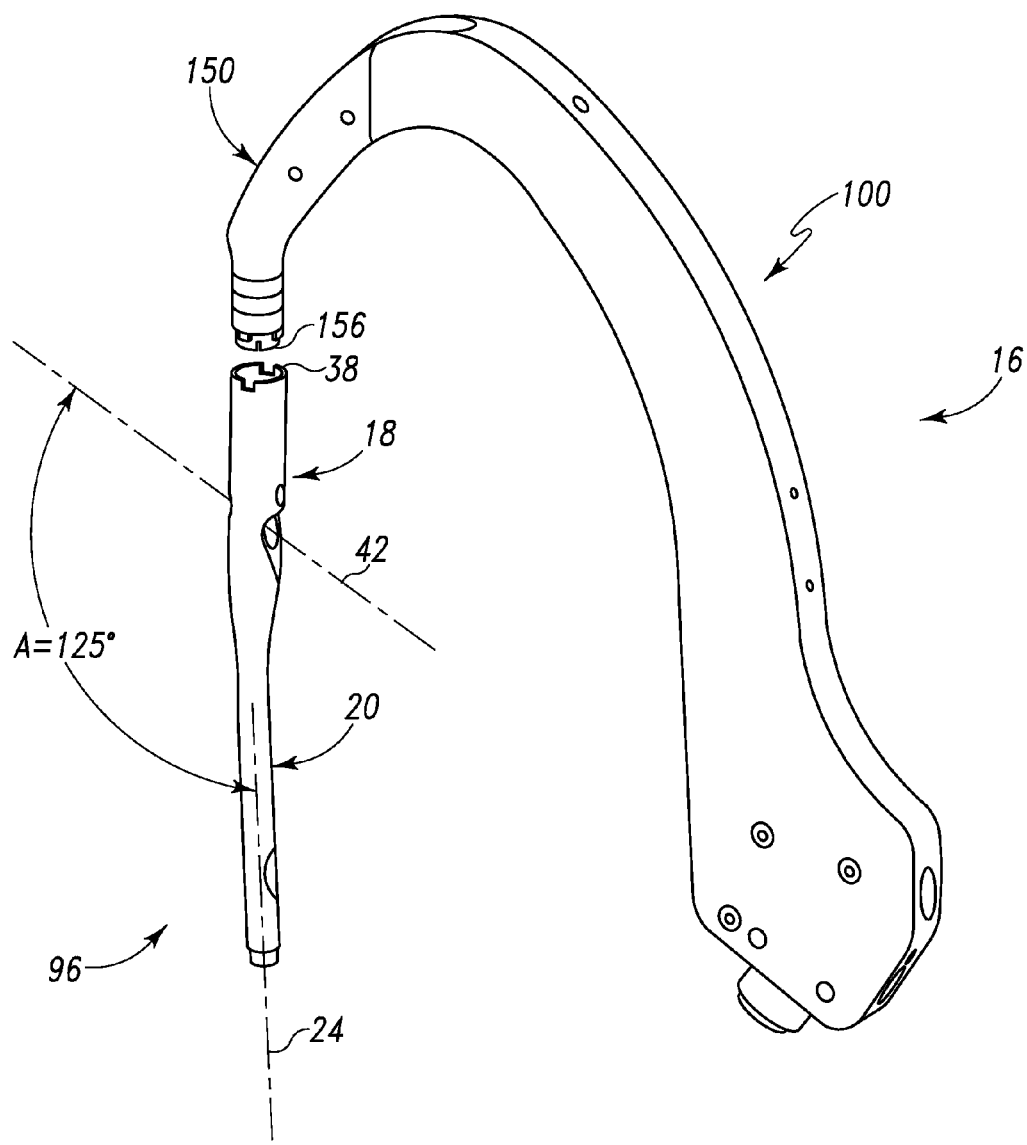
FIG. 13A is a perspective view of a first target jig in connecting alignment with a first IM nail, and is part of an HFN set.
Figure 13B:
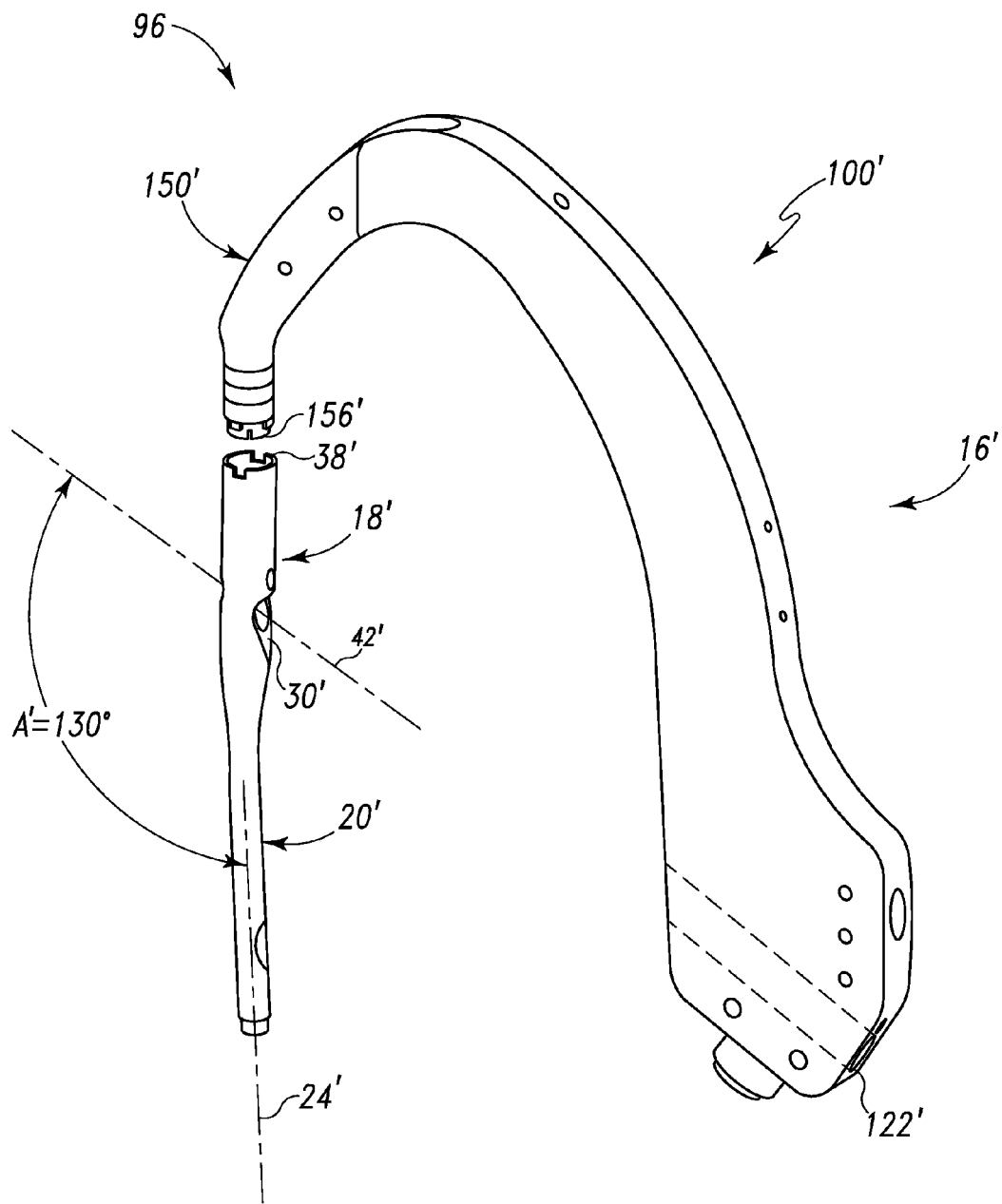
FIG. 13B is a second target jig in connecting alignment with a second IM nail, and is also part of the HFN set of FIG. 13A.

FIGS. 13A & 13B depict an HFN set 96. FIG. 13A shows a first HFN system 16 and FIG. 13B shows a second HFN system 16'. (HFN system 16 of FIG. 5A and all of its elements are identical to first HFN system 16 of FIG. 13A and all of its elements. Therefore, the numbering of all the elements has been retained, but many of the names of the elements are now preceded by the word "first".) First HFN system 16 includes a first HFN prosthesis 18 and a second HFN prosthesis 18'. First HFN prosthesis 18 includes a first IM nail 20 and a first target jig 100. The angle between a distal shaft portion 24 of a first IM nail 20 and a first lag screw axis 42, indicated by the letter A in FIG. 13A, is equal to approximately 125 degrees, This angle corresponds to patients who have a femoral neck-diaphysis angle of approximately 125 degrees. Second HFN prosthesis 18' includes a second IM nail 20' and a second target jig 100'. The angle between a second distal shaft portion 24' of IM nail 20' and a second lag screw axis 42', indicated by the letter A' in FIG. 13, is equal to approximately 130 degrees. This corresponds to patients who have a femoral neck-diaphysis angle of approximately 130 degrees. As described similarly for FIG. 5A, first lag screw axis 42' is the common axis of a first lag target hole 122' of first target jig 100' and a first lag screw hole 30' of first IM nail 20', when first target jig 100' and first IM nail 20' are attached together.

HFN set 96 also may include tower extension assembly 128 (previously described for FIG. 5A) and target tube assembly 60 (previously described for FIG. 8), both of which may be used with each of first HFN system 16 and second HFN system 16'.

Second target jig 100' should not be used with first IM nail 20 because first lag screw hole 30 of first IM nail 20 and second lag target hole 122' of second target jig 100' would not have a common lag screw axis. Without a common lag screw axis, it is impossible to insert target tube assembly 60 (see FIG. 7) and drill the pilot hole for lag screw 40. All the other target holes and guide wire holes of target jig 100' would also be slightly misdirected for use with IM nail 20. Therefore, HFN system 16 is provided with a IM nail attachment arrangement that prevents mismatching, i.e., attaching IM nail 20 to target jig 100'. This arrangement also prevents attaching IM nail 20' to target jig 100. As described next for FIGS. 14-19, nose connector 156 of target jig 100 has a different configuration than nose connector 156' of target jig 100'. Similarly, nail connector 38 has a different configuration than nail connector 38'.

Figure 14:
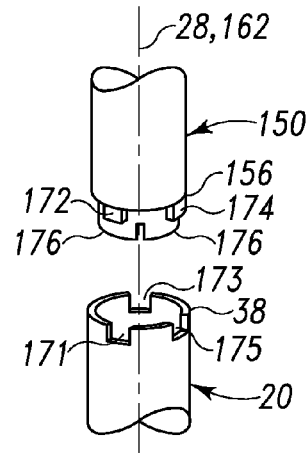
FIG. 14 is a detailed, perspective view of a first nose connector of the first target jig shown in FIG. 13A, shown in connecting alignment with a first nail connector of the first IM nail.
Figure 15:
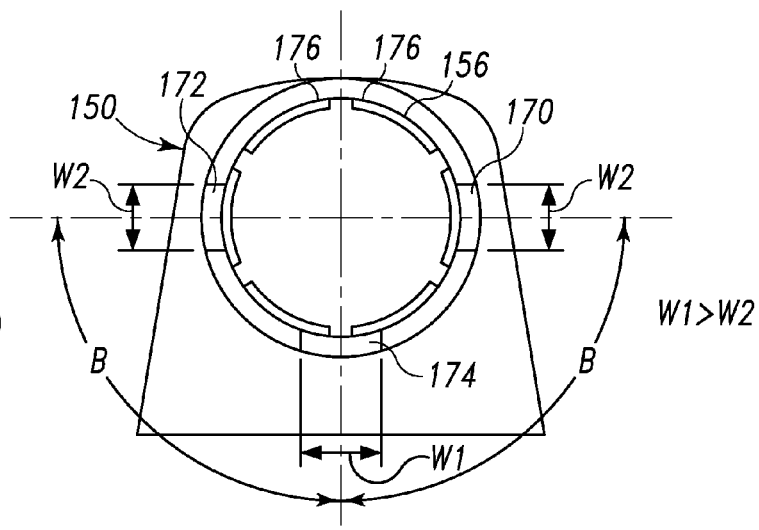
FIG. 15 is a detailed, end view of the first nose connector shown in FIG. 14.
Figure 16:
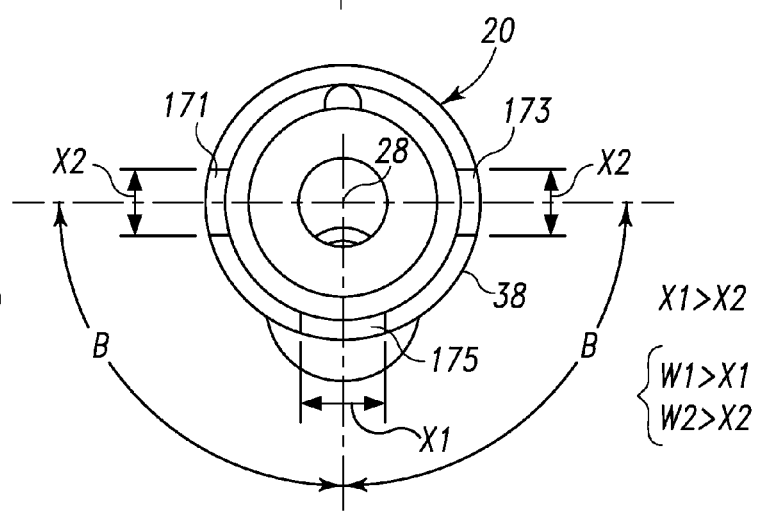
FIG. 16 is a detailed, end view of the first nail connector shown in FIG. 14.
Figure 17:
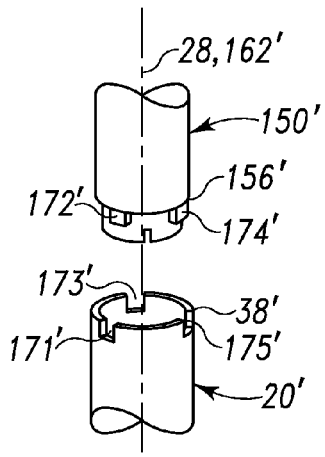
FIG. 17 is a detailed, perspective view of a second nose connector of the second target jig shown in FIG. 13B, shown in connecting alignment with a second nail connector of the second IM nail.
Figure 18:
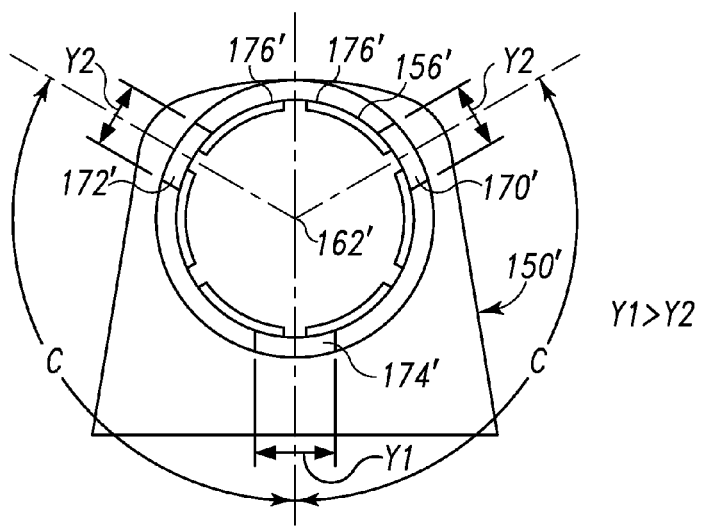
FIG. 18 is a detailed, end view of the second nose connector shown in FIG. 17.
Figure 19:
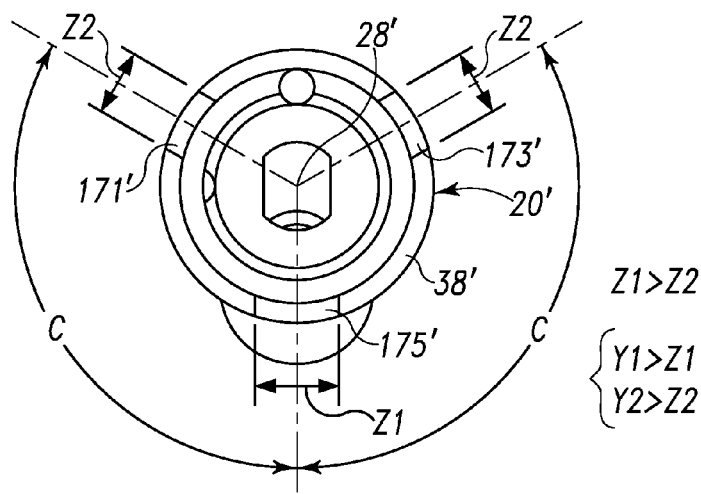
FIG. 19 is a detailed, end view of the second nail connector shown in FIG. 17.

FIG. 14 is a detailed, perspective view of a first nose connector 156 of a first nose component 150 shown in connecting alignment with a first nail connector 38 of first IM nail 20. FIG. 15 is a detailed, end view of first nose connector 156 and FIG. 16 is a detailed, end view of first nail connector 38. FIG. 17 is a detailed, perspective view of a second nose connector 156' of a second nose component 150' shown in connecting alignment with a second nail connector 38' of second IM nail 20'. FIG. 18 is a detailed, end view of second nose connector 156' and FIG. 19 is a detailed, end view of second nail connector 38'.

As shown in FIG. 15, first nose connector 156 of first nose component 150 includes a plurality of spring fingers 176 equally spaced apart and forming a circle centered on axis 162. Each of spring fingers 176 are sized and configured to deflect and then to grip the inside of first IM nail 20, but only when inserted to a desired depth. The axial force required to removably connect first nose component 150 to first IM nail 20 may be predetermined by adjustment of the overall spring rate of the individual spring fingers 176. As is well known in the art, various mechanical attachment designs are possible to provide the desired holding force at the desired insertion depth. For example, an annular recess (not shown) on the inside of first IM nail 20 may be provided to retain annular ridges (not shown) on the ends of spring fingers 176.

As shown in FIG. 15, first nose connector 156 includes a first flute 170, a second flute 172 and a third flute 174 spaced radially apart around axis 162. First and second flutes, 170 and 172, have a width W2. Third flute has a width W1, which is slightly greater than W2. First and second flutes, 170 and 172, are equally spaced apart from third flute 174 along the perimeter of nose component 150 by an angle indicated by the letter B. As shown in FIG. 16, first nail connector 38 of IM nail 20 includes a first recess 171, a second recess 173 and a third recess 175. First and second recesses, 171 and 173, have a width X2, which is slightly greater than width W2 of first and second flutes, 170 and 172. Third recess 175 has a width X1, which is slightly greater than width W1 of third flute 174. First and second recesses, 171 and 173, are equally spaced apart from third recess 175 along the perimeter of IM nail 20 by angle B. Only when third flute 174 of nose connector 156 is radially aligned with third recess 175 of first nail connector 38 and axis 162 of first nose component 162 is coaxial with axis 28 of IM nail 20, first nail connector 38 may receive first nose connector 156 to the desired depth to allow first IM nail 20 and first nose component 150 to be removably connected.

As shown in FIG. 118, second nose connector 156' of second nose component 150' includes a plurality of spring fingers 176' equally spaced apart and forming a circle centered on axis 162'. Each of spring fingers 176' are sized and configured to deflect and then to grip the inside of second IM nail 20', but only when inserted to a desired depth. The axial force required to removably connect second nose component 150' to IM nail 20' may be predetermined by adjustment of the overall spring rate of the individual spring fingers 176'. As for the first HFN system 16, various mechanical attachment designs are possible to provide the desired holding force at the desired insertion depth.

As shown in FIG. 18, second nose connector 156' includes a first flute 170', a second flute 172' and a third flute 174' spaced radially apart around axis 162'. First and second flutes, 170' and 172', have a width Y2. Third flute has a width Y1, which is slightly greater than Y2. First and second flutes, 170' and 172', are equally spaced apart from third flute 174' along the perimeter of nose component 150' by an angle C. As shown in FIG. 19, second nail connector 38' of IM nail 20' includes a first recess 171', a second recess 173' and a third recess 175'. First and second recesses, 171' and 173', have a width Z2, which is slightly greater than width Y2 of first and second flutes, 170' and 172'. Third recess 175' has a width Z1, which is slightly greater than width Y1 of third flute 174'. First and second recesses, 171' and 173', are equally spaced apart from third recess 175' along the perimeter of IM nail 20' by angle C. Only when third flute 174' of second nose connector 156' is radially aligned with third recess 175' of second nail connector 38' and axis 162' of second nose component 162' is coaxial with axis 28' of second IM nail 20', second nail connector 38' may receive second nose connector 156' to the desired depth to allow second IM nail 20' and second nose component 150' to be removably connected.

Because angle B of first nose connector 156 and first nail connector 28 is not equal to angle C of second nose connector 156' and second nail connector 28', it is impossible to connect first nose connector 156 to second nail connector 28' or to connect second nose connector 156' to first nail connector 28. This connecting arrangement also insures that each of first IM nail 20 and second IM nail 20' are removably connected to each of target jig 100 and target jig 100', respectively, in the proper orientation for insertion into the femur of the patient.

We have shown and described various embodiments and examples. However, one of ordinary skill in the art can accomplish further adaptations of the methods and devices described herein by appropriate modifications without departing from the overall concept. We have mentioned several of such potential modifications and others will be apparent to those skilled in the art. For instance, the specific materials, dimensions and the scale of drawings should be understood to be non-limiting examples. Accordingly, we do not intend the scope of the following claims to be understood as limited to the details of structure, materials or acts shown and described in the specification and drawings.

The invention claimed is:

1. A method of implanting an internal fixation prosthesis in a patient during a surgical procedure for repairing a fractured bone, the method comprising:
   a. obtaining an instrument system comprising:
      i. a target wire;
      ii. a handle formed from a radio translucent material having a target hole for guided passage of the target wire along a target axis, whereby the target axis coincides with the intersection of a first plane and a second plane orthogonal to the first plane;
      iii. a nose component attached to an end of the handle and removably connectable to the prosthesis, the nose component including an alignment sight formed from a radio-opaque material;
      whereby when the prosthesis is connected to the nose component and the target wire is positioned through the target hole along the target axis, the image of the target wire may be radioscopically viewed along a first line of sight contained in the first plane to bisect the image of the alignment device, thereby providing a first visual reference to the user for directing the target wire into the desired portion of the bone while holding the prosthesis in a desired position relative to the bone;
   b. removably connecting the prosthesis to the nose component of the instrument system;
   c. initially positioning the prosthesis relative to the fractured bone;
   d. inserting the target wire into the target hole along the target axis;
   e. radioscopically obtaining the first visual reference;
   f. manipulating the instrument until the target wire is directed into a desired portion of the bone;
   g. inserting the target wire into a desired portion of the fractured bone;
   h. obtaining a cannulated drill; and
   i. drilling a pilot hole along the target axis into the bone to a desired depth into the desired portion of the fractured bone, wherein the pilot hole is sized for receiving the lag screw.

2. The method of claim 1, further including:
   a. obtaining an extension assembly removably attachable to the handle, the extension assembly including:
      i. a tower having a pair of spaced-apart, parallel channels defining a pair of channel axes, such that when the tower is attached to the handle, both channel axes lie in the second plane and are offset from the target axis;
      ii. a first alignment wire and a second alignment wire, each of which is sized for guided passage through one of the channels;
      whereby when the tower is attached to the handle and each of the first and second alignment wires is inserted into one of the channels, the image of the first alignment wire obstructs the image of the second alignment wire when radioscopically viewed along a second line of sight contained in the second plane, thereby providing a second visual reference to the user for directing the target wire into the desired portion of the bone;
   b. removably attaching the extension assembly to the handle; and
   c. radioscopically obtaining the second visual reference.

3. The method of claim 1, wherein the alignment sight comprises a pair of spaced-apart, opposing arms defining a U-shaped gap therebetween when radioscopically viewed along the first line of sight, whereby the target wire may be radioscopically viewed to extend centered between and parallel to the opposing arms when the full width of the gap is radioscopically viewable.

4. A method of repairing a fractured, proximal femur, the method comprising:
   a. obtaining a hip fracture nail system for the internal fixation of a fractured, proximal femur of a surgical patient, the hip fracture nail system comprising:
      i. an intramedullary nail for implantation into the intramedullary canal of the proximal femur of the patient, the intramedullary nail including a distal shaft portion defining a distal shaft axis and a proximal shaft portion containing a lag screw hole defining a lag screw axis that is transverse to the distal shaft axis;
      ii. a lag screw for implantation into the neck and head of the fractured, proximal femur, the lag screw including a proximal portion retainable in the lag screw hole and extending along the lag screw axis, and a distal portion for anchoring into the head;
      iii. a target jig including:
         1. a handle having an inferior end, a superior end and a lag target hole defining a lag target axis, wherein the intersection of a medial-lateral plane and an anterior-posterior plane coincides with the lag target axis; and
         2. a nose component formed from a radio-opaque material and attached to the superior end of the handle, the nose component including an alignment sight, wherein the nose component is removably connectable to the proximal shaft portion of the intramedullary nail, such that the lag target axis is coaxial with the lag screw axis; and
      iv. a target wire for insertion through the lag target hole and into the femoral head along the lag screw axis for guiding a cannulated drill;
      such that when the intramedullary nail is connected to the target jig and inserted into the intramedullary canal of the proximal femur and the target wire is at least partially inserted through the lag target hole, a first visual reference is observable in which the alignment sight and the target wire are radioscopically viewable along a first line of sight contained in the medial-lateral plane when the image of the target wire is centered on the image of the alignment device;
   b. removably connecting the nail to the nose component of the target jig;
   c. initially positioning the nail inside the intramedullary canal of the proximal, fractured femur;
   d. inserting the target wire into the lag target hole along the lag target axis;
   e. radioscopically observing the first visual reference;
   f. manipulating the instrument until the target wire is directed into a desired portion of the bone;
   g. inserting the target wire into the desired portion of the fractured bone;
   h. obtaining a cannulated drill; and
   i. drilling a bore along the target axis into the bone to a desired depth while the target wire is inserted into the desired portion of the fractured bone.

5. The method of claim 4, wherein the alignment sight comprises a pair of spaced-apart, opposing arms defining a U-shaped gap therebetween when radioscopically viewed along the first line of sight, whereby the first guide wire may be radioscopically viewed to extend centered between and parallel to the opposing arms when the full width of the gap is radioscopically viewable.

6. The method of claim 4, further including:
a. obtaining an extension assembly removably attachable to the target jig, the extension assembly including:
  i. a tower having a pair of spaced-apart, parallel channels defining a pair of channel axes offset from the lag target axis, such that when the tower is attached to the target jig, the pair of channel axes lie in the anterior-posterior plane;
  ii. a first alignment wire and a second alignment wire, each of which is sized for guided passage through one of the channels;
  such that when the intramedullary nail is connected to the target jig and inserted into the intramedullary canal of the proximal femur, and the tower is attached to the target jig and each of the first and second alignment wires is inserted into one of the channels, a second visual reference is observable in which the image of the first alignment wire obstructs the image of the second alignment wire when viewed in the anterior-posterior plane on the radioscopic imaging device; and
b. radioscopically observing the second visual reference.

* * * * *